(12) United States Patent
Hayashi et al.

(10) Patent No.: US 11,261,422 B2
(45) Date of Patent: Mar. 1, 2022

(54) CULTURE MEDIUM COMPOSITION FOR SUSPENSION CULTURE ALLOWING EASY CELL RECOVERY, AND CELL RECOVERY METHOD

(71) Applicant: NISSAN CHEMICAL CORPORATION, Tokyo (JP)

(72) Inventors: Hisato Hayashi, Funabashi (JP); Ayako Aihara, Shiraoka (JP); Daisuke Hatanaka, Funabashi (JP)

(73) Assignee: NISSAN CHEMICAL CORPORATION, Tokyo (JP)

(*) Notice: Subject to any disclaimer, the term of this patent is extended or adjusted under 35 U.S.C. 154(b) by 425 days.

(21) Appl. No.: 16/082,929

(22) PCT Filed: Mar. 8, 2017

(86) PCT No.: PCT/JP2017/009154
§ 371 (c)(1),
(2) Date: Sep. 6, 2018

(87) PCT Pub. No.: WO2017/154952
PCT Pub. Date: Sep. 14, 2017

(65) Prior Publication Data
US 2019/0071635 A1    Mar. 7, 2019

(30) Foreign Application Priority Data
Mar. 9, 2016  (JP) .............................. JP2016-046365

(51) Int. Cl.
*C12N 5/00* (2006.01)
*C09D 105/04* (2006.01)

(52) U.S. Cl.
CPC ......... *C12N 5/0018* (2013.01); *C09D 105/04* (2013.01); *C12N 5/0068* (2013.01); *C12N 2500/10* (2013.01); *C12N 2500/34* (2013.01); *C12N 2513/00* (2013.01); *C12N 2533/70* (2013.01); *C12N 2533/74* (2013.01); *C12N 2533/80* (2013.01); *C12N 2537/10* (2013.01)

(58) Field of Classification Search
None
See application file for complete search history.

(56) References Cited

U.S. PATENT DOCUMENTS

| | | | |
|---|---|---|---|
| 2017/0002311 A1 | 1/2017 | Otani et al. | |
| 2017/0009201 A1* | 1/2017 | Hayashi | C12M 25/16 |
| 2018/0008646 A1* | 1/2018 | Ishii | C12N 5/0068 |

FOREIGN PATENT DOCUMENTS

| | | | |
|---|---|---|---|
| EP | 2878664 A1 | 6/2015 | |
| EP | 2889368 A1 | 7/2015 | |
| EP | 3252151 A1 | 12/2017 | |
| JP | 2014-079171 A | 5/2014 | |
| JP | 2014-236698 A | 12/2014 | |
| WO | WO 2014/017513 A1 | 1/2014 | |
| WO | WO 2014/030726 A1 | 2/2014 | |
| WO | WO 2015/111685 A1 | 7/2015 | |
| WO | WO 2015/111686 A1 | 7/2015 | |
| WO | WO 2016/039391 A1 | 3/2016 | |
| WO | WO 2016121896 | * 8/2016 | |
| WO | WO 2018/079797 A1 | 5/2018 | |

OTHER PUBLICATIONS

European Patent Office, Extended European Search Report in European Patent Application No. 17763292.4 (dated Nov. 21, 2018).
Aihara et al., "Saisei Iryo no Hatten ni Matareru Sanjigen Saibo Baiyo-yo no Baichi, Ashiba Zairyo Kaihatsu—Sanjigen Baiyo Baichi no Kaihatsu Jirei-," *Material Stage*, 15(11): 11-15 (2016).
Japanese Patent Office, International Search Report in International Patent Application No. PCT/JP2017/009154 (dated Apr. 11, 2017).

* cited by examiner

*Primary Examiner* — Maria G Leavitt
(74) *Attorney, Agent, or Firm* — Leydig, Voit & Mayer, Ltd.

(57) ABSTRACT

The present invention provides a medium composition containing deacylated gellan gum or a salt thereof, and an acidic polysaccharide or a salt thereof capable of maintaining a random coil state in a divalent metal cation medium and cross-linking via a divalent metal ion, and permitting culture of a cell or a tissue in suspension, wherein a concentration of the deacylated gellan gum or a salt thereof in the medium composition is 0.002-0.01 (w/v) %, a concentration of the acidic polysaccharide or a salt thereof is 0.004-0.1 (w/v) %, and a mass ratio of the acidic polysaccharide or a salt thereof to the deacylated gellan gum or a salt thereof is not less than 1. In addition, the present invention provides a method for isolating a cell or tissue from a culture preparation containing the medium composition and cell or tissue, including applying a shear force to the culture preparation.

4 Claims, No Drawings

CULTURE MEDIUM COMPOSITION FOR SUSPENSION CULTURE ALLOWING EASY CELL RECOVERY, AND CELL RECOVERY METHOD

CROSS-REFERENCE TO RELATED APPLICATIONS

This patent application is the U.S. national phase of International Patent Application No. PCT/JP2017/009154, filed Mar. 8, 2017, which claims the benefit of Japanese Patent Application No. 2016-046365, filed on Mar. 9, 2016, which are incorporated by reference in their entireties herein.

TECHNICAL FIELD

The present invention relates to a medium composition for suspension culture permitting easy cell recovery, and a method for recovering cells from a cell culture containing the medium composition.

BACKGROUND ART

Polysaccharides such as deacylated gellan gum (DAG) and the like form a three-dimensional network (amorphous structure) in water by assembling via a metal cation (e.g., divalent metal cation such as calcium ion and the like). When cells are cultured in a liquid medium containing the three-dimensional network, the cells in the medium are trapped in the three-dimensional network and do not sink. Therefore, the cells can be cultured while being floated and uniformly dispersed in a suspended state without the need for shaking, rotational manipulation and the like (static suspension culture). In addition, it is possible to form the aforementioned three-dimensional network without substantially increasing the viscosity of the liquid medium. Therefore, a medium composition containing the three-dimensional network is also superior in the operability in passaging and the like (patent document 1). This medium composition permitting static suspension culture has various superior properties such as promotion of proliferation activity of various cells and the like. Thus, its application to a wide range of technical fields such as regenerative medicine, large-scale production of protein and the like, and the like is expected.

DOCUMENT LIST

Patent Document patent document 1: WO 2014/017513

SUMMARY OF INVENTION

Technical Problem

The present inventors noted such problem that when cells or tissues are cultured using a medium composition containing deacylated gellan gum (DAG) and permitting static suspension culture and the cells or tissues are recovered from the culture by centrifugation, the cells and tissues do not precipitate sufficiently due to the effect of the medium composition to maintain the suspended state of the cells or tissues and the recovery rate remains low.

The present invention aims to provide a composition for suspension culture permitting easy cell recovery, a method for recovering cells from a cell culture containing the medium composition and the like.

Solution to Problem

The present inventors have conducted intensive studies in an attempt to solve the above-mentioned problems. The effect of maintaining the suspended state of the cells or tissues is produced by the three-dimensional network (amorphous structure) formed by an assembly of deacylated gellan gum via a metal cation (e.g., divalent metal cation such as calcium ion and the like). Therefore, they considered that cells or tissues can be quickly precipitated and the recovery rate can be improved by destroying the three-dimensional network to lose the effect of maintaining the suspended state of the cells or tissues immediately before recovery of the cells or tissues from the culture by centrifugation after completion of the suspension culture. They tried to destroy the above-mentioned three-dimensional network by applying a shear force to the medium composition by an operation such as pipetting, filter filtration and the like after static suspension culture of the cells in a medium composition containing deacylated gellan gum (DAG) alone as polysaccharide and capable of static suspension culture. As a result, the cell recovery rate was improved to a certain degree but it was not sufficiently satisfactory. Thus, they studied the components of the medium composition and found that addition of a particular concentration of sodium alginate to the medium in addition to the deacylated gellan gum achieves superior property that the effect of maintaining the suspended state of the cells or tissues in static culture is retained and that the effect of maintaining the suspended state of the cells or tissues rapidly disappears by adding a chelating agent as necessary and applying a shear force by pipetting, filter filtration and the like (vulnerability of the effect of maintaining the suspended state of the cells or tissues to shear force). Using the medium composition containing deacylated gellan gum and sodium alginate, long-term static suspension culture of cells and tissues was possible. Furthermore, cells and tissues could be recovered in a high yield by quickly losing the effect of maintaining the suspended state of the cells and tissues by a comparatively easy operation such as pipetting, filter filtration and the like and then subjecting the cells and tissues to centrifugation. Deacylated gellan gum has a constituent unit with a comparatively linear structure, and a plurality of deacylated gellan gum chains bundle in the medium composition to form a tight and stable three-dimensional network. As a result, the three-dimensional network is difficult to destroy by pipetting, filter filtration and the like, thus causing a decrease in the cell recovery rate. On the other hand, when alginic acid having a relatively bulky structure due to the inclusion of both uronic acids of α1-4-bonded L-glucuronic acid and β1-4-bound D-mannuronic acid is added to the medium composition, the concentration of deacylated gellan gum in the medium composition can be reduced relatively, as well as bundling of the deacylated gellan gum is suppressed. This in turn enables easy destruction of the three-dimensional network by applying a shear force by pipetting, filter filtration and the like, possibly leading to a rapid loss of the effect of maintaining the suspended state of the cells or tissues and improvement of the cell recovery rate. Based on these findings, the present inventors studied further and completed the present invention.

That is, the present invention provides the following.

[1] A medium composition permitting culture of a cell or a tissue in suspension, comprising deacylated gellan gum or a salt thereof, and an acidic polysaccharide or a salt thereof capable of maintaining a random coil state in a divalent metal cation medium and cross-linking via a divalent metal ion, wherein a concentration of the deacylated gellan gum or a salt thereof in the medium composition is 0.002-0.01 (w/v) %, a concentration of the aforementioned acidic polysaccharide or a salt thereof is 0.004-0.1 (w/v) %, and a mass ratio of the aforementioned acidic polysaccharide or a salt thereof to the deacylated gellan gum or a salt thereof is not less than 1.

[2] The medium composition of [1], wherein the aforementioned acidic polysaccharide is selected from the group consisting of alginic acid, pectin and pectic acid.

[3] The medium composition of [2], wherein the aforementioned acidic polysaccharide is alginic acid.

[4] The medium composition of any of [1] to [3], further comprising a metal cation.

[5] The medium composition of [4], wherein the aforementioned metal cation is a calcium ion.

[6] The medium composition of any of [1] to [5], wherein the aforementioned acidic polysaccharide or a salt thereof is treated by high-pressure vapor sterilization.

[7] A cell or tissue culture preparation comprising the medium composition of any of [1] to [6], and a cell or a tissue.

[8] A method for culturing a cell or a tissue, comprising culturing the cell or tissue in the medium composition of any of [1] to [6].

[9] A method for isolating a cell or tissue from the culture preparation of [7], comprising applying a shear force to the culture preparation.

[10] The method of [9], wherein the shear force is applied to the culture preparation by pipetting or filter filtration.

[11] The method of [9] or [10], further comprising adding a chelating agent to the culture preparation.

[12] The method of any of [9] to [11], further comprising subjecting the culture preparation to centrifugation after applying the shear force.

Advantageous Effects of Invention

The medium composition of the present invention has an effect of maintaining the suspended state of cells or tissues and has property of rapidly losing the effect by adding a chelating agent as necessary, and applying a shear force by pipetting, filter filtration and the like. Therefore, using the medium composition of the present invention, cells and tissues can be suspension cultured (preferably, static suspension culture), and the cells and tissues can be recovered at a high recovery rate from the obtained culture preparation. Particularly, cells and tissues can be recovered at a high recovery rate while maintaining the volume of the obtained culture preparation, that is, without diluting the culture preparation with a medium solution, a buffer, water or the like.

DESCRIPTION OF EMBODIMENTS

The present invention is described in more detail below.
Medium Composition

The present invention provides a medium composition enabling culturing cells or tissues in suspension. The medium composition enables culturing desired cells or a tissue containing the same while maintaining the suspending state.

The cell in the present invention is a most basic unit constituting animals or plants, which has, as its elements, cytoplasm and various organelles inside the cellular membrane. In this case, the nucleus encapsulating the DNA may or may not be contained intracellularly. For example, the animal-derived cells in the present invention include reproductive cells such as spermatozoon, oocyte and the like, somatic cells constituting the living body, stem cells, progenitor cells, cancer cells separated from the living body, cells separated from the living body, which acquired immortalizing ability and is maintained stably in vitro (cell line), cells separated from the living body and applied with artificial genetic modification, cells separated from the living body wherein the nucleus is artificially exchanged, and the like. Examples of the somatic cells constituting the living body include, but are not limited to, fibroblast, bone marrow cells, B lymphocytes, T lymphocytes, neutrophils, red blood cells, platelets, macrophages, monocytes, osteocytes, bone marrow cells, pericytes, dendritic cells, keratinocytes, adipocytes, mesenchymal cells, epithelial cells, epidermal cells, endothelial cells, vascular endothelial cells, hepatocytes, chondrocytes, cumulus cells, nerve system cells, glial cells, neurons, oligodendrocytes, microglia, astrocytes, heart cells, esophagus cells, myocytes (e.g., smooth muscle cells or skeletal muscle cells), pancreatic beta cells, melanin cells, hematopoietic progenitor cells, mononuclear cells and the like. The somatic cells include cells collected from any tissue, for example, skin, kidney, spleen, adrenal gland, liver, lung, ovary, pancreas, uterus, stomach, colon, small intestine, large intestine, spleen, bladder, prostate, testis, thymus, muscle, connective tissue, bone, cartilage, vascularized tissue, blood, heart, eye, brain, nerve tissue and the like. Stem cells are cells concurrently having an ability to replicate itself, and an ability to differentiate into other plural lineages. Examples thereof include, but are not limited to, embryonic stem cells (ES cell), embryonic tumor cells, embryonic reproductive stem cells, artificial pluripotent stem cells (iPS cell), neural stem cells, hematopoietic stem cells, mesenchymal stem cells, liver stem cells, pancreas stem cells, muscle stem cells, reproductive stem cells, intestinal stem cells, cancer stem cells, hair follicle stem cells and the like. Progenitor cells are cells on the way to differentiate from the aforementioned stem cell into a particular somatic cell or reproductive cell. Cancer cells are cells that are derived from a somatic cell and have acquired infinite proliferative capacity. Cell lines are cells that have acquired infinite proliferative capacity by an artificial operation in vitro, and examples thereof include, but are not limited to, CHO (Chinese hamster ovary cell line), HCT116, Huh7, HEK293 (human embryonic kidney cell), HeLa (human uterine cancer cell line), HepG2 (human liver cancer cell line), UT7/TPO (human leukemia cell line), MDCK, MDBK, BHK, C-33A, HT-29, AE-1, 3D9, Ns0/1, Jurkat, NIH3T3, PC12, S2, Sf9, Sf21, High Five (registered trade mark), Vero and the like.

The plant-derived cell in the present invention also includes cells separated from each tissue of a plant body, as well as a protoplast obtained by artificially removing the cell wall from the cell.

The tissue in the present invention is a unit of a structure which is an assembly in a certain manner of cells having some kinds of different properties and functions, and examples of the animal tissue include epithelial tissue, connective tissue, muscular tissue, nerve tissue and the like. Examples of the plant tissue include meristem, epidermis tissue, assimilation tissue, mesophyll tissue, conductive tissue, mechanical tissue, parenchyma tissue, dedifferentiated cell cluster (callus) and the like.

When cells or tissues are cultured, the cells or tissues to be cultured can be selected freely from the cells or tissues described above and cultured. The cells or tissues can be directly recovered from an animal or plant body. The cells or tissues may be induced, grown or transformed from an animal or plant body by applying a particular treatment and then collected. In this case, the treatment may be in vivo or in vitro. Examples of the animal include fish, amphibian, reptiles, birds, pancrustacea, hexapoda, mammals and the like. Examples of the mammal include, but are not limited to, rat, mouse, rabbit, guinea pig, squirrel, hamster, vole, platypus, dolphin, whale, dog, cat, goat, bovine, horse, sheep, swine, elephant, common marmoset, squirrel monkey, *Macaca mulatta*, chimpanzee and human. The plant is not particularly limited as long as the collected cells or tissues can be applied to liquid culture. Examples thereof include, but are not limited to, plants producing crude drugs (e.g., saponin, alkaloids, berberine, scopolin, phytosterol etc.) (e.g., *ginseng*, periwinkle, henbane, coptis, *belladonna* etc.), plants producing dye or polysaccharide to be a starting material for cosmetic or food (e.g., anthocyanin, safflower dye, madder dye, saffron dye, flavones etc.) (e.g., blueberry, safflower, madder, saffron etc.), or plants producing a pharmaceutical drug substance and the like.

Suspending of cells or tissues in the present invention refers to a state where cells or tissues do not adhere to a culture container (non-adhesive). Furthermore, in the present invention, when the cells or tissues are cultured, the state where the cells or tissues are uniformly dispersed and suspended in the liquid medium composition in the absence of a pressure on or vibration of the liquid medium composition from the outside or shaking, rotating operation and the like in the composition is referred to as "static suspension", and cultivation of the cells or tissues in such condition is referred to as "static suspension culture". In the "static suspension", the period of suspending includes not less than 5 min (e.g., at least 5-60 min), not less than 1 hr (e.g., 1 hr-24 hr), not less than 24 hr (e.g., 1 day-21 days), not less than 48 hr, not less than 7 days etc., though the period is not limited thereto as long as the suspended state is maintained.

The medium composition of the present invention permits static suspension of cells and/or tissues at least on one point in the temperature range capable of maintaining or culturing cells or tissues (e.g., 0-40° C.). The medium composition to be used in the present invention permits static suspension of cells and/or tissues at least on one point in the temperature range of preferably 25-37° C., most preferably 37° C.

Whether static suspension is possible can be evaluated by, for example, uniformly dispersing the cells to be cultured in a medium composition to be evaluated at a concentration of $2 \times 10^4$ cells/ml, injecting 10 ml thereof in a 15 ml conical tube, standing the tube for at least not less than 5 min (e.g., not less than 1 hr, not less than 24 hr, not less than 48 hr, not less than 7 days) at 37° C., and observing whether the suspended state of the cells is maintained. When not less than 70% of the total cells are in a suspended state, it is concluded that the suspended state was maintained. Polystyrene beads (Size 500-600 μm, manufactured by Polysciences Inc.) may be used for evaluation instead of the cells The medium composition of the present invention contains deacylated gellan gum or a salt thereof, and alginic acid or a salt thereof. The medium composition of the present invention containing deacylated gellan gum or a salt thereof, and alginic acid or a salt thereof is provided with the property enabling suspension culture (preferably, static suspension culture) of cells and tissues (effect of maintaining the suspended state of cells or tissues).

The deacylated gellan gum is a linear polymer polysaccharide containing 4 molecules of sugars of 1-3 bonded glucose, 1-4 bonded glucuronic acid, 1-4 bonded glucose and 1-4 bonded rhamnose as the constituent unit, which is a polysaccharide represented by the following formula (I) wherein $R_1$, $R_2$ are each a hydrogen atom, and n is an integer of two or more. $R_1$ may contain a glyceryl group, $R_2$ may contain an acetyl group, and the content of the acetyl group and glyceryl group is preferably not more than 10%, more preferably not more than 1%.

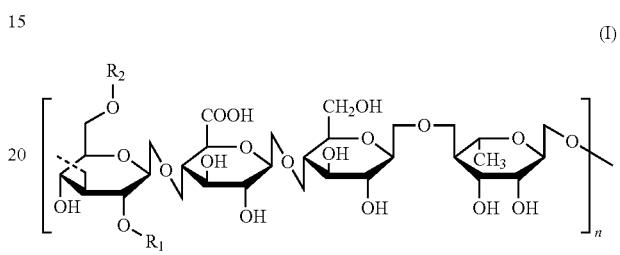

(I)

Deacylated gellan gum can be produced by culturing a gellan gum producing microorganism in a fermentation medium, subjecting a mucosal product produced outside fungal body to an alkali treatment, deacylating and recovering the glyceryl group and the acetyl group bonded to 1-3 bonded glucose residue and, after steps of drying, pulverization and the like, powderizing the product. Examples of the purification method include liquid-liquid extraction, fractional precipitation, crystallization, various kinds of ion exchange chromatography, gel filtration chromatography using Sephadex LH-20 and the like, adsorption chromatography using activated carbon, silica gel and the like, adsorption and desorption treatment of active substance by thin layer chromatography, high performance liquid chromatography using reversed-phase column and the like, and impurity can be removed and the compound can be purified by using them singly or in combination in any order, or repeatedly. Examples of the gellan gum-producing microorganism include, but are not limited to, *Sphingomonas elodea* and microorganisms obtained by modifying the gene of *Sphingomonas elodea*.

As the deacylated gellan gum, a phosphorylated one can also be used. The phosphorylation can be performed by a known method.

A deacylated gellan gum derivative of a compound represented by the formula (I) wherein a hydroxyl group for $R_1$ and/or $R_2$ is substituted by $C_{1-3}$ alkoxy group, $C_{1-3}$ alkylsulfonyl group, a monosaccharide residue such as glucose, fructose and the like, oligosaccharide residue such as sucrose, lactose and the like, or amino acid residue such as glycine, arginine and the like can also be used in the present invention. In addition, the deacylated gellan gum can also be crosslinked using a crosslinker such as 1-ethyl-3-(3-dimethylaminopropyl)carbodiimide (EDC) and the like.

Examples of the salt include alkali metal salts such as lithium, sodium, potassium; alkaline earth metal salts such as calcium, barium, magnesium; salts such as aluminum, zinc, copper, iron and the like; ammonium salt; quaternary ammonium salts such as tetraethylammonium, tetrabutylammonium, methyltributylammonium, cetyltrimethylammonium, benzylmethylhexyldecylammonium, choline and the like; salts with organic amines such as pyridine, triethylamine, diisopropylamine, ethanolamine, diolamine, trometh-amine, meglumine, procaine, chloroprocaine and the like; salts with amino acid such as glycine, alanine, valine and the like; and the like.

The weight average molecular weight of deacylated gellan gum or a salt thereof is preferably 10,000 to 50,000,000, more preferably 100,000 to 20,000,000, still more preferably 1,000,000 to 10,000,000. For example, the molecular weight can be measured based on pullulan by gel penetration chromatography (GPC).

As deacylated gellan gum or a salt thereof, commercially available products, for example, "KELCOGEL (registered trade mark of CP Kelco) CG-LA" manufactured by SAN-SHO Co., Ltd., "KELCOGEL (registered trade mark of CP Kelco)" manufactured by San-Ei Gen F.F.I., Inc. and the like can be used.

Alginic acid is a polysaccharide having a structure in which both uronic acids of α1-4 bonded L-glucuronic acid and β1-4 bonded D-mannuronic acid are straight-chain polymerized.

Alginic acid and a salt thereof can be extracted and purified from brown algae represented by kelp and wakame by an ion exchange reaction of a carboxyl group of alginic acid. The alginic acid in the alga body is in an insoluble salt with polyvalent cation such as calcium ion and the like. Thus, this is ion exchanged with Na to give water-soluble sodium alginate which is extracted outside the alga body. Furthermore, an acid is added to an aqueous solution of sodium alginate to cause coagulation and precipitation of insoluble alginic acid, and the coagulated and precipitated alginic acid is isolated to give purified alginic acid.

Examples of the salt include alkali metal salts such as lithium, sodium, potassium; alkaline earth metal salts such as calcium, barium, magnesium; salts such as aluminum, zinc, copper, iron and the like; ammonium salt; quaternary ammonium salts such as tetraethylammonium, tetrabutylammonium, methyltributylammonium, cetyltrimethylammonium, benzylmethylhexyldecylammonium, choline and the like; salts with organic amines such as pyridine, triethylamine, diisopropylamine, ethanolamine, diolamine, trometh-amine, meglumine, procaine, chloroprocaine and the like; salts with amino acid such as glycine, alanine, valine and the like; and the like. In the present invention, sodium alginate is preferably used from the aspect of solubility in water.

The weight average molecular weight of alginic acid or a salt thereof is preferably 300 to 50,000,000, more preferably 500 to 10,000,000, still more preferably 1,000 to 5,000,000. For example, the molecular weight can be measured based on pullulan by gel penetration chromatography (GPC).

As alginic acid or a salt thereof, a commercially available product, for example, the following product can also be used.

KIMICA Corporation:
  KIMICA Alginic Series IL-2, IL-6, I-1, I-3, I-5, I-8, ULV-L3, ULV-L5, ULV-1, ULV-3, ULV-5, ULV-20, ULV-L3G, IL-6G, I-1G, I-3G, IL-6M, BL-2, BL-6, B-1, B-3, B-5, B-8, SKAT-ONE, SKAT-ULV
  Algitechs Series LL, L, M, H
Kikkoman Biochemifa Company:
  DUCK ALGIN NSPH2R, NSPHR, NSPMR, NSPLR, NSPLLR SANSHO Co., Ltd.:
  SUKOGIN, SAN-ALGIN
Hokkaido Mitsui Chemicals, Inc.:
  Alginic Acid Oligosaccharide ALGIN Alginic acid is an acidic polysaccharide capable of maintaining a random coil state in a divalent metal cation medium and being crosslinked via a divalent metal ion. It is expected that the same effect as that of the medium composition of the present invention can be provided even when an acidic polysaccharide or a salt thereof other than alginic acid capable of maintaining a random coil state in a divalent metal cation medium and being crosslinked via a divalent metal ion is used in place of alginic acid or a salt thereof. As the acidic polysaccharide capable of maintaining a random coil state in a divalent metal cation medium and being crosslinked via a divalent metal ion, alginic acid, pectin, pectic acid and the like can be mentioned. As the divalent metal cation, calcium ion, magnesium ion, barium ion, copper ion, iron ion, zinc ion, tin ion, lead ion and the like can be mentioned. The present invention also encompasses an embodiment in which an acidic polysaccharide or a salt thereof other than alginic acid capable of maintaining a random coil state in a divalent metal cation medium and being crosslinked via a divalent metal ion is used in place of alginic acid or a salt thereof.

Deacylated gellan gum and alginic acid may be present in the form of tautomer, geometric isomer, a mixture of tautomers and geometric isomers, or mixtures thereof formed by isomerization in the ring or outside the ring. When the deacylated gellan gum and alginic acid has an asymmetric center, irrespective of whether the compound is formed by isomerization, it may be present in the form of a resolved optical isomer or a mixture containing same at any ratio.

Deacylated gellan gum or a salt thereof, and alginic acid or a salt thereof form a three-dimensional network (amorphous structure) by assembling via a metal cation (e.g., divalent metal cation such as calcium ion and the like) when mixed with a liquid medium. It is known that polysaccharides form a microgel via a metal cation (e.g., JP-A-2004-129596), and the aforementioned amorphous structure also includes such microgel as one embodiment. One embodiment of the assembly of deacylated gellan gum or a salt thereof, and alginic acid or a salt thereof via a metal cation is a film structure. The medium composition of the present invention contains a three-dimensional network (amorphous structure) formed by an assembly of deacylated gellan gum or a salt thereof, and alginic acid or a salt thereof via a metal cation (e.g., divalent metal cation such as calcium ion and the like). When cells or tissues are cultured in the medium composition of the present invention, the cells or tissues suspended in the medium composition are trapped in the three-dimensional network and do not form sediments. Therefore, the cells or tissues can be cultured while being uniformly dispersed in a suspended state (static suspension culture) without the need for shaking, rotational manipulation and the like. The medium composition of the present invention in a preferable embodiment contains the aforementioned three-dimensional network (amorphous structure) in a uniformly dispersed state.

In a preferable embodiment, formation of the above-mentioned three-dimensional network (amorphous structure) does not substantially increase the viscosity of the medium composition of the present invention. The "without substantially increasing the viscosity of the medium composition" means that the viscosity of the medium composition does not exceed 8 mPa·s. In this case, the viscosity of the liquid medium composition is not more than 8 mPa·s, preferably not more than 4 mPa·s, more preferably not more than 2 mPa·s, at 37° C.

The viscosity of the medium composition can be measured, for example, by the method described in the below-mentioned Examples. Specifically, it can be measured under 37° C. conditions and using an E-type viscosity meter (manufactured by Toki Sangyo Co., Ltd., TV-22 type viscosity meter, model: TVE-22 L, corn roter: standard roter 1° 34'×R24, rotating speed 100 rpm).

The medium composition of the present invention may contain a polysaccharide or a salt thereof other than "deacylated gellan gum or a salt thereof, and alginic acid or a salt thereof". The polysaccharide is preferably an acidic polysaccharide having an anionic functional group. The acidic polysaccharide is not particularly limited as long as it has an anionic functional group in the structure thereof, and includes, for example, polysaccharides having a uronic acid (e.g., glucuronic acid, iduronic acid, galacturonic acid, mannuronic acid), polysaccharides having a sulfuric acid group or a phosphoric acid group in a part of the structure thereof, and polysaccharides having the both structures, and includes not only naturally-obtained polysaccharides but also polysaccharides produced by microorganisms, polysaccharides produced by genetic engineering, and polysaccharides artificially synthesized using an enzyme. More specifically, examples thereof include hyaluronic acid, native gellan gum, rhamsan gum, diutan gum, xanthan gum, carageenan, xanthan gum, hexuronic acid, fucoidan, pectin, pectic acid, pectinic acid, heparan sulfate, heparin, heparitin sulfate, keratosulfate, chondroitin sulfate, dermatan sulfate, rhamnan sulfate and a salt thereof.

The concentration of deacylated gellan gum or a salt thereof in the medium composition of the present invention is, for example, 0.002-0.01 (w/v) %, preferably 0.002-0.009 (w/v) %, more preferably 0.003-0.009 (w/v) %.

The concentration of alginic acid or a salt thereof in the medium composition of the present invention is, for example, 0.004-0.1 (w/v) %, preferably 0.004-0.02 (w/v) %, more preferably 0.004-0.015 (w/v) %, further preferably 0.005-0.015 (w/v) %.

The concentration of the deacylated gellan gum or a salt thereof is preferably not less than 0.002 (w/v) %, preferably not less than 0.003 (w/v) %, to ensure a sufficient action to suspend the cells or tissues. On the other hand, when the concentration is too high, the suspending action may become strong to lower the cell recovery rate and handling property of the medium itself. Therefore, it is not more than 0.01 (w/v) %, preferably not more than 0.009 (w/v) %. The concentration of alginic acid or a salt thereof is not less than 0.004 (w/v) %, preferably not less than 0.005 (w/v) %, to ensure the property to afford rapid disappearance of the effect of maintaining the suspended state of the cells or tissues by a shear force (vulnerability of the effect of maintaining the suspended state of the cells or tissues to shear force). On the other hand, when the concentration is too high, gelling may occur. It is not more than 0.1 (w/v) %, preferably not more than 0.02 (w/v) %, more preferably not more than 0.015 (w/v) %.

The mass ratio of the deacylated gellan gum or a salt thereof and alginic acid or a salt thereof contained in the medium composition of the present invention is not less than 1 part by mass, preferably not less than 2 parts by mass, of alginic acid or a salt thereof per 1 part by mass of deacylated gellan gum or a salt thereof, to achieve the property of rapidly losing the effect of maintaining the suspended state of the cells or tissues by a shear force. In one embodiment, for example, 1-4 parts by mass, preferably 1-3 parts by mass, more preferably 1-2 parts by mass, of alginic acid or a salt thereof is used per 1 part by mass of deacylated gellan gum or a salt thereof.

The concentration of the compound in the medium composition can be calculated by the following formula.

$$\text{Concentration [\% (W/V)]} = \text{weight (g) of compound} / \text{volume (ml) of medium composition} \times 100$$

The medium composition of the present invention containing deacylated gellan gum or a salt thereof, and alginic acid or a salt thereof at the above-mentioned contents affords the effect of maintaining the suspended state of the cells or tissues. In addition, the medium composition of the present invention containing deacylated gellan gum or a salt thereof, and alginic acid or a salt thereof at the above-mentioned contents has property of rapidly losing the effect of maintaining the suspended state of the cells or tissues by a shear force such as pipetting, filter filtration and the like (vulnerability of the effect of maintaining the suspended state of the cells or tissues to shear force).

The medium composition of the present invention contains the three-dimensional network (amorphous structure) formed by an assembly of deacylated gellan gum or a salt thereof, and alginic acid or a salt thereof via a metal cation (e.g., divalent metal cation such as calcium ion and the like), and this affords the effect of maintaining the suspended state of the cells or tissues. Due to the presence of alginic acid or a salt thereof, the three-dimensional network is fragile to a chelating agent or shear force and the three-dimensional network is easily destroyed by a shear force by pipetting, filter filtration and the like. As a result, the effect of maintaining the suspended state of the cells or tissues is rapidly lost. Deacylated gellan gum contains a constituent unit having a comparatively linear structure. A plurality of deacylated gellan gum chains are bundled in the medium composition to form a tight and stable three-dimensional network. This three-dimensional network is difficult to be destroyed by chelating agent, pipetting, filter filtration and the like. In contrast, when alginic acid having a comparatively bulky structure due to the presence of both uronic acids of $\alpha$1-4 bonded L-glucuronic acid and $\beta$1-4 bonded D-mannuronic acid is added to the medium composition, bundling of the deacylated gellan gum is suppressed. As a result, the three-dimensional network is considered to become fragile to a shear force by pipetting, filter filtration and the like, though not particularly bound by the theory. Therefore, the present invention may be considered as a method for promoting vulnerability of the three-dimensional network (amorphous structure) formed by an assembly of deacylated gellan gum or a salt thereof via a metal cation (e.g., divalent metal cation such as calcium ion and the like) in the medium composition to a shear force, comprising adding alginic acid or a salt thereof to the medium composition.

As mentioned above, when deacylated gellan gum or a salt thereof, and alginic acid or a salt thereof are mixed with a liquid medium, they assemble via a metal cation (e.g., divalent metal cation such as calcium ion and the like) in the liquid medium to form a three-dimensional network (amorphous structure). Thus, the medium composition in the present invention contains metal cations, for example, divalent metal cations (calcium ion, magnesium ion, zinc ion, iron ion and copper ion etc.), preferably calcium ion. Two or more kinds of metal cations can be used in combination, for example, calcium ion and magnesium ion, calcium ion and zinc ion, calcium ion and iron ion, and calcium ion and copper ion. Those of ordinary skill in the art can appropriately determine the combination. The metal cation concentration in the medium composition of the present invention is, but is not limited to, 0.1 mM-300 mM, preferably 0.5 mM-100 mM. The metal cation may be mixed with a medium, or a salt solution may be separately prepared and added to the medium.

The loss of the effect of maintaining the suspended state of the cells or tissues by a shear force by pipetting, filter filtration and the like is a reversible reaction. Fragments of the three-dimensional network (amorphous structure) destroyed by the shear force assemble again via a metal cation (e.g., divalent metal cation such as calcium ion and the like) and regenerate a three-dimensional network (amorphous structure).

The medium composition of the present invention can be prepared by mixing a medium (preferably liquid medium) used for culturing cells or tissues with deacylated gellan gum or a salt thereof, and alginic acid or a salt thereof.

Examples of the medium used in culturing cells or tissues derived from animal (e.g., mammal) include Dulbecco's Modified Eagle's Medium (DMEM), hamF12 medium (Ham's Nutrient Mixture F12), DMEM/F12 medium, McCoy's 5A medium, Eagle MEM medium (Eagle's Minimum Essential Medium; EMEM), αMEM medium (alpha Modified Eagle's Minimum Essential Medium; αMEM), MEM medium (Minimum Essential Medium), RPMI1640 medium, Iscove's Modified Dulbecco's Medium (IMDM), MCDB131 medium, William medium E, IPL41 medium, Fischer's medium, StemPro34 (manufactured by Invitrogen), X-VIVO 10 (manufactured by Cambrex Corporation), X-VIVO 15 (manufactured by Cambrex Corporation), HPGM (manufactured by Cambrex Corporation), StemSpan H3000 (manufactured by STEMCELL Technologies), StemSpanSFEM (manufactured by STEMCELL Technologies), StemlineII (manufactured by Sigma Aldrich), QBSF-60 (manufactured by Qualitybiological), StemPro hESC SFM (manufactured by Invitrogen), mTeSR1 or 2 medium (manufactured by STEMCELL Technologies), Sf-900II (manufactured by Invitrogen), Opti-Pro (manufactured by Invitrogen), and the like.

When the cells or tissues are derived from a plant, a medium obtained by adding auxins and, where necessary, a plant growth control substance (plant hormone) such as cytokinins and the like at a suitable concentration to a basic medium such as Murashige Skoog (MS) medium, Linsmaier Skoog (LS) medium, White medium, Gamborg's B5 medium, niche medium, hela medium, Morel medium and the like generally used for culture of plant tissues, or a modified medium wherein these medium components are modified to an optimal concentration (e.g., ammonia nitrogen at a half concentration etc.) can be mentioned as the medium. These media can be further supplemented, where necessary, with casein degrading enzyme, corn steep liquor, vitamins and the like. Examples of the auxins include, but are not limited to, 3-indoleacetic acid (IAA), 3-indolebutyric acid (IBA), 1-naphthaleneacetic acid (NAA), 2,4-dichlorophenoxyacetic acid (2,4-D) and the like. For example, auxins can be added to a medium at a concentration of about 0.1-about 10 ppm. Examples of the cytokinins include, but are not limited to, kinetin, benzyladenine (BA), zeatin and the like. For example, cytokinins can be added to a medium at a concentration of about 0.1-about 10 ppm.

Those of ordinary skill in the art can freely add, according to the object, sodium, potassium, calcium, magnesium, phosphorus, chlorine, various amino acids, various vitamins, antibiotic, serum, fatty acid, sugar and the like to the above-mentioned medium. For culture of animal-derived cells and/or tissues, those of ordinary skill in the art can also add, according to the object, one or more kinds of other chemical components and biogenic substances in combination. Examples of the components to be added to a medium for animal-derived cells and/or tissues include fetal bovine serum, human serum, horse serum, insulin, transferrin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various hormones, various growth factors, various extracellular matrices, various cell adhesion molecules and the like. Examples of the cytokine to be added to a medium include, but are not limited to, interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-18 (IL-18), interleukin-21 (IL-21), interferon-α (IFN-α), interferon-β (IFN-β), interferon-γ (IFN-γ), granulocyte colony stimulating factor (G-CSF), monocyte colony stimulating factor (M-CSF), granulocyte-macrophage colony stimulating factor (GM-CSF), stem cell factor (SCF), flk2/flt3 ligand (FL), leukemia cell inhibitory factor (LIF), oncostatin M (OM), erythropoietin (EPO), thrombopoietin (TPO) and the like.

Examples of the hormone to be added to a medium include, but are not limited to, melatonin, serotonin, thyroxine, triiodothyronine, epinephrine, norepinephrine, dopamine, anti-Mullerian hormone, adiponectin, adrenocorticotropic hormone, angiotensinogen and angiotensin, antidiuretic hormone, atrial natriuretic peptide, calcitonin, cholecystokinin, corticotropin release hormone, erythropoietin, follicle stimulating hormone, gastrin, ghrelin, glucagon, gonadotropin release hormone, growth hormone release hormone, human chorionic gonadotropin, human placental lactogen, growth hormone, inhibin, insulin, insulin-like growth factor, leptin, luteinizing hormone, melanocyte stimulating hormone, oxytocin, parathyroid hormone, prolactin, secretin, somatostatin, thrombopoietin, thyroid-stimulating hormone, thyrotropin releasing hormone, cortisol, aldosterone, testosterone, dehydroepiandrosterone, androstenedione, dihydrotestosterone, estradiol, estrone, estriol, progesterone, calcitriol, calcidiol, prostaglandin, leukotriene, prostacyclin, thromboxane, prolactin releasing hormone, lipotropin, brain natriuretic peptide, neuropeptide Y, histamine, endothelin, pancreas polypeptide, rennin and enkephalin.

Examples of the growth factor to be added to a medium include, but are not limited to, transforming growth factor-α (TGF-α), transforming growth factor-β (TGF-β), macrophage inflammatory protein-1α (MIP-1a), epithelial cell growth factor (EGF), fibroblast growth factor-1, 2, 3, 4, 5, 6, 7, 8 or 9 (FGF-1, 2, 3, 4, 5, 6, 7, 8, 9), nerve cell growth factor (NGF) hepatocyte growth factor (HGF), leukemia inhibitory factor (LIF), protease nexin I, protease nexin II, platelet-derived growth factor (PDGF), cholinergic differentiation factor (CDF), chemokine, Notch ligand (Delta1 and the like), Wnt protein, angiopoietin-like protein 2, 3, 5 or 7 (Angpt2, 3, 5, 7), insulin like growth factor (IGF), insulin-like growth factor binding protein-1 (IGFBP), Pleiotrophin and the like.

In addition, these cytokines and growth factors having amino acid sequences artificially altered by gene recombinant techniques can also be added. Examples thereof include IL-6/soluble IL-6 receptor complex, Hyper IL-6 (fusion protein of IL-6 and soluble IL-6 receptor) and the like.

Examples of the various extracellular matrices and various cell adhesion molecules include collagen I to XIX, fibronectin, vitronectin, laminin-1 to 12, nitogen, tenascin, thrombospondin, von Willebrand factor, osteopontin, fibrinogen, various elastins, various proteoglycans, various cadherins, desmocolin, desmoglein, various integrins, E-selectin, P-selectin, L-selectin, immunoglobulin superfamily, matrigel, poly-D-lysine, poly-L-lysine, chitin, chitosan, sepharose, hyaluronic acid, alginate gel, various hydrogels, cleavage fragments thereof and the like.

Examples of the antibiotic to be added to a medium include Sulfonamides, penicillin, phenethicillin, methicillin, oxacillin, cloxacillin, dicloxacillin, flucloxacillin, nafcillin, ampicillin, penicillin, amoxicillin, ciclacillin, carbenicillin, ticarcillin, piperacillin, azlocillin, mezlocillin, mecillinam, andinocillin, cephalosporin and a derivative thereof, oxolinic acid, amifloxacin, temafloxacin, nalidixic acid, piromidic acid, ciprofloxacin, cinoxacin, norfloxacin, perfloxacin, Rosaxacin, ofloxacin, enoxacin, pipemidic acid, sulbactam, clavulanic acid, β-bromopenisillanic acid, β-chloropenisillanic acid, 6-acetylmethylene-penisillanic acid, cephoxazole, sultampicillin, adinoshirin and sulbactam formaldehyde hudrate ester, tazobactam, aztreonam, sulfazethin, isosulfazethin, norcardicin, m-carboxyphenyl, phenylacetamidophosphonic acid methyl, chlortetracycline, oxytetracycline, tetracycline, demeclocycline, doxycycline, methacycline, and minocycline.

In a preferable embodiment, the medium (preferably, liquid medium) contains metal cations, for example, divalent metal cations (calcium ion, magnesium ion, zinc ion, iron ion and copper ion etc.), preferably calcium ion. This aims to form, upon mixing with a liquid medium, a three-dimensional network (amorphous structure) of deacylated gellan gum or a salt thereof, and alginic acid or a salt thereof via a metal cation (e.g., divalent metal cation such as calcium ion and the like) in the liquid medium. The concentration of metal cation (preferably calcium ion) in the medium is not particularly limited as long as it is a concentration sufficient for deacylated gellan gum or a salt thereof, and alginic acid or a salt thereof to assemble via the metal cation and form a three-dimensional network (amorphous structure). For example, it is 0.1 mM to 300 mM, preferably 0.5 mM to 100 mM. A medium containing the metal cation and deacylated gellan gum or a salt thereof, and alginic acid or a salt thereof may be mixed, or a medium free of the metal cation and deacylated gellan gum or a salt thereof, and alginic acid or a salt thereof are mixed, and thereafter, an aqueous solution of a metal cation prepared separately may be added to the mixture.

When deacylated gellan gum or a salt thereof, and alginic acid or a salt thereof are added to the above-mentioned medium, deacylated gellan gum or a salt thereof, and alginic acid or a salt thereof are first dissolved or dispersed in an appropriate solvent (to be a medium additive). Thereafter, the medium additive is added to the medium such that the final concentrations of deacylated gellan gum or a salt thereof, and alginic acid or a salt thereof in the medium composition fall within the concentrations described in detail above. A medium additive containing deacylated gellan gum or a salt thereof, and a medium additive containing alginic acid or a salt thereof may be prepared separately, and each may be added to the medium, or a medium additive containing both deacylated gellan gum or a salt thereof, and alginic acid or a salt thereof (i.e., mixture of deacylated gellan gum or a salt thereof, and alginic acid or a salt thereof) may be prepared and added to the medium. Preferably, a medium additive containing both deacylated gellan gum or a salt thereof, and alginic acid or a salt thereof (i.e., mixture of deacylated gellan gum or a salt thereof, and alginic acid or a salt thereof) may be prepared and added to the medium.

Here, examples of an appropriate solvent used for preparation of the medium additive include, but are not limited to, aqueous solvents such as water, dimethyl sulfoxide (DMSO), various alcohols (e.g., methanol, ethanol, butanol, propanol, glycerin, propylene glycol, butyleneglycol and the like), and the like. In this case, the concentrations of deacylated gellan gum or a salt thereof, and alginic acid or a salt thereof in the medium additive are desirably, for example, about 10- to 500-fold, preferably about 25- to 100-fold, concentration of the final concentration of the medium composition described in detail above.

Deacylated gellan gum or a salt thereof, and alginic acid or a salt thereof may be sterilized as necessary. The sterilization method is not particularly limited, and, for example, radiation sterilization, ethylene oxide gas sterilization, high-pressure vapor sterilization (autoclave sterilization), filter sterilization and the like can be mentioned. When filter sterilization (hereinafter sometimes to be referred to as filtration sterilization) is to be performed, the material of the filter part is not particularly limited and, for example, glass fiber, nylon, PES (polyethersulfone), hydrophilic PVDF (polyvinylidene fluoride), cellulose mixed ester, celluloseacetate, polytetrafluoroethylene and the like can be mentioned. While the size of the pore in the filter is not particularly limited, it is preferably 0.1 μm to 10 μm, more preferably 0.1 μm to 1 μm, most preferably 0.1 μm to 0.5 μm. These sterilization treatments can be applied regardless of whether the deacylated gellan gum or a salt thereof, and alginic acid or a salt thereof are in a solid state or in a solution state.

The temperature of the high-pressure vapor sterilization treatment is generally 105-135° C., preferably 115° C.-130° C., more preferably 118-123° C. (e.g., 121±1° C.). The pressure in the sterilization treatment is generally 0.12-0.32 MPa, preferably 0.17-0.27 MPa, more preferably 0.19-0.23 MPa (e.g., 0.21±0.1 MPa). The sterilization treatment time is generally 1-60 min, preferably 5-45 min, more preferably 15-25 min (e.g., 20±1 min).

The combination of the high-pressure vapor sterilization treatment conditions is,
for example, 105-135° C., 0.12-0.32 MPa, 1-60 min;
preferably 115° C.-130° C., 0.17-0.27 MPa, 5-45 min;
more preferably 118-123° C. (e.g., 121±1° C.), 0.19-0.23 MPa (e.g., 0.21±0.1 MPa), 15-25 min (e.g., 20±1 min).

By adding a solution or dispersion solution of deacylated gellan gum or a salt thereof, and alginic acid or a salt thereof to a liquid medium in the above-mentioned preparation, deacylated gellan gum or a salt thereof, and alginic acid or a salt thereof assemble via a metal cation (e.g., divalent metal cation such as calcium ion and the like) in the liquid medium, whereby a three-dimensional network (amorphous structure) is formed and the medium composition of the present invention can be obtained. Media generally contain a metal cation (e.g., calcium ion) at a concentration sufficient to produce an assembly of deacylated gellan gum or a salt thereof, and alginic acid or a salt thereof to form a three-dimensional network (amorphous structure). Thus, the medium composition of the present invention can be obtained by simply adding deacylated gellan gum or a salt thereof, and alginic acid or a salt thereof or a dispersion solution thereof to a liquid medium. Alternatively, a medium may be added to the medium additive (solution or dispersion solution of deacylated gellan gum or a salt thereof, and alginic acid or a salt thereof) of the present invention. Furthermore, the medium composition of the present invention can also be prepared by mixing deacylated gellan gum or a salt thereof, and alginic acid or a salt thereof and a medium component (a powder medium or concentrated medium) in an aqueous solvent (e.g., water including ion exchanged water, ultrapure water and the like). Examples of the embodiment of mixing include, but are not limited to, (1)

mixing a liquid medium and a medium additive (solution), (2) adding a solid (powder etc.) of deacylated gellan gum or a salt thereof, and alginic acid or a salt thereof to a liquid medium, (3) mixing a medium additive (solution) and a powder medium, (4) mixing powder medium and a solid (powder etc.) of deacylated gellan gum or a salt thereof, and alginic acid or a salt thereof with an aqueous solvent, and the like. To prevent distribution of deacylated gellan gum or a salt thereof, and alginic acid or a salt thereof in a medium composition from being non-uniform, the embodiment of (1) is preferable.

When deacylated gellan gum or a salt thereof and alginic acid or a salt thereof are dissolved in a solvent (e.g., aqueous solvent such as water, liquid medium and the like), or deacylated gellan gum or a salt thereof, and alginic acid or a salt thereof, and a powder medium are dissolved in a solvent, the mixture may be heated to promote dissolution. Examples of the heat temperature include 80° C.-130° C., preferably 100° C.-125° C. (e.g., 121° C.) at which heating sterilization is performed. After heating, the obtained solution of deacylated gellan gum or a salt thereof and alginic acid or a salt thereof is cooled to room temperature. By adding the aforementioned metal cations (e.g., divalent metal cations such as calcium ion and the like) to the solution (e.g., adding the solution to liquid medium), deacylated gellan gum or a salt thereof, and alginic acid or a salt thereof assemble via a metal cation (e.g., divalent metal cation such as calcium ion and the like), thus forming a three-dimensional network (amorphous structure), and the medium composition of the present invention can be obtained. Alternatively, a three-dimensional network (amorphous structure) can also be formed by dissolving deacylated gellan gum or a salt thereof, and alginic acid or a salt thereof in a solvent (e.g., aqueous solvent such as water, liquid medium and the like) containing the aforementioned metal cations (e.g., divalent metal cations such as calcium ion and the like) with heating (e.g., 80° C.-130° C., preferably 100° C.-125° C. (e.g., 121° C.)), and cooling the obtained solution to room temperature.

The deacylated gellan gum or a salt thereof has a constituent unit having a comparatively linear structure and plural sugar chains are bundled when added to a solvent (e.g., water) and is not dissolved easily. However, when alginic acid or a salt thereof is added, bundling of deacylated gellan gum or a salt thereof is suppressed due to the comparatively bulky structure involving both uronic acids of α1-4 bonded L-glucuronic acid and β1-4 bonded D-mannuronic acid, and deacylated gellan gum or a salt thereof is dissolved comparatively easily. Therefore, deacylated gellan gum or a salt thereof and alginic acid or a salt thereof can be dissolved in a solvent (e.g., aqueous solvent such as water, liquid medium and the like) at a comparatively low temperature (e.g., 0-37° C., preferably, 10-30° C.) without heating.

Examples of the production method of the medium composition of the present invention are shown below, which are not to be construed as limitative.

Deacylated gellan gum or a salt thereof, and alginic acid or a salt thereof are added to ion exchange water or ultrapure water. Then, they are stirred at a temperature at which deacylated gellan gum or a salt thereof and alginic acid or a salt thereof can be dissolved (e.g., 5-60° C., preferably 5-40° C., more preferably 10-30° C.) to allow for dissolution to a transparent state.

After dissolving, the mixture is allowed to cool with stirring as necessary, and sterilized (e.g., autoclave sterilization at 121° C. for 20 min, filter filtration). The aforementioned sterilized aqueous solution is added with stirring (e.g., homomixer etc.) to a given medium to be used for static culture to uniformly mix the solution with the medium. The mixing method of the aqueous solution and the medium is not particularly limited, and may be manual mixing such as pipetting etc., or mixing with an instrument such as magnetic stirrer, mechanical stirrer, homomixer and homogenizer.

For uniform dispersing of deacylated gellan gum or a salt thereof and alginic acid or a salt thereof in a liquid medium, for example, the liquid medium is placed in a conical tube, stirring is maintained by vortex and the like, and an aqueous solution of deacylated gellan gum or a salt thereof and alginic acid or a salt thereof is vigorously flushed into the liquid medium with a syringe with a syringe needle. Using a medium preparation kit (Nissan Chemical Industries FCeM™-series Preparation Kit), the medium composition of the present invention in which a three-dimensional network (amorphous structure) formed by an assembly of deacylated gellan gum or a salt thereof, and alginic acid or a salt thereof via a metal cation (e.g., divalent metal, cation such as calcium ion and the like) is uniformly dispersed can be prepared with ease.

The medium composition of the present invention may be filtrated through a filter after mixing. The size of the pore of the filter to be used for the filtration treatment is 5 μm to 100 μm, preferably 5 μm to 70 μm, more preferably 10 μm to 70 μm.

Culture Method of Cell or Tissue

The present invention provides a method for culturing cells or tissues comprising culturing the cells or tissues in the above-mentioned medium composition of the present invention. Furthermore, the present invention also provides a culture preparation containing the medium composition of the present invention obtained by the culture method of the present invention and the like and cells or tissues. The culture preparation refers to a resultant product obtained by culturing cells or tissues, and contains the cells or tissues, a medium (medium composition) and, in some cases, cell-secretory components and the like.

The medium composition of the present invention contains a three-dimensional network (amorphous structure) formed by an assembly of deacylated gellan gum or a salt thereof, and alginic acid or a salt thereof via a metal cation (e.g., divalent metal cation such as calcium ion and the like). When cells or tissues are cultured in the medium composition of the present invention, the cells or tissues suspended in the medium composition are trapped in the three-dimensional network and do not form sediments. Therefore, the cells or tissues can be cultured while being uniformly dispersed in a suspended state (static suspension culture) without the need for shaking, rotational manipulation and the like. Therefore, the culture method of the present invention may be a method for suspension culture (preferably, static suspension culture) of cells or tissues.

As mentioned above, the loss of the effect of maintaining the suspended state of the cells or tissues by a shear force by pipetting, filter filtration and the like is a reversible reaction. Even when a three-dimensional network (amorphous structure) formed by an assembly of deacylated gellan gum or a salt thereof, and alginic acid or a salt thereof via a metal cation (e.g., divalent metal cation such as calcium ion and the like) is destroyed by a shear force by pipetting, filter filtration and the like at the time of start of the suspension culture when cells and tissues are suspended in the medium composition of the present invention, when the culture is left standing, the fragments of the destroyed three-dimensional network (amorphous structure) assemble again via a metal cation (e.g., divalent metal cation such as calcium ion and the like) and regenerate a three-dimensional network (amorphous structure) to afford again the effect of maintaining the suspended state of the cells or tissues. Therefore, dispersed cells or tissues can be continuously subjected to static suspension culture.

The period of suspending cells or tissues in static suspension culture is not less than 5 min (e.g., at least 5-60 min), not less than 1 hr (e.g., 1 hr-24 hr), not less than 24 hr (e.g., 1 day-21 days), not less than 48 hr, not less than 7 days or the like. These periods are not limited as long as a suspended state is maintained.

When cells or tissues are cultured in the medium composition of the present invention, the cells or tissues prepared separately are added to the culture composition of the present invention and mixed to give a uniform dispersion. In this case, the mixing method is not particularly limited and, for example, manual mixing using pipetting and the like, mixing using instrument such as stirrer, vortex mixer, microplate mixer, shaking machine and the like can be mentioned. After mixing, the culture medium may be stood still, or the culture medium may be rotated, shaken or stirred as necessary. The rotating speed and frequency can be appropriately set according to the object of those of ordinary skill in the art.

When the medium composition needs to be exchanged during the static culture period, the cells or tissues and the medium composition are separated by centrifugation or filtration treatment, cells or tissues are recovered and a fresh medium composition of the present invention can be added to the recovered cells or tissues. Alternatively, the cells or tissues are appropriately concentrated by centrifugation or filtration treatment, and a new medium composition can be added to the concentrated liquid. For example, unlimitatively, the gravitational acceleration (G) of centrifugation is 10G to 400G, and the size of the pore of the filter used for the filtration treatment is 10 μm to 100 μm. In addition, using magnetic fine particles coated, on the surface, with an antibody that specifically binds to the object cell, cultured cells and/or tissues can be separated by magnetic force. Examples of such magnetic fine particles include Dynabeads (manufactured by Veritas Ltd.), MACS microbead (manufactured by Miltenyi Biotec), BioMag (manufactured by Techno Chemicals Corporation) and the like. The cells or tissues may be recovered by the below-mentioned method of the present invention for recovering cells or tissues. The medium composition of the present invention containing alginic acid or a salt thereof in addition to deacylated gellan gum or a salt thereof affords the effect of maintaining the suspended state of the cells or tissues and has property of rapidly losing the effect by adding a chelating agent as necessary and applying a shear force by pipetting, filter filtration and the like. Therefore, using the medium composition of the present invention, cells and tissues can be suspension cultured (preferably static suspension culture), the cells can be recovered in a high yield from the obtained culture preparation by a centrifugation operation, and passaged with high efficiency while suppressing the loss of cells.

The temperature when cells or tissues are cultivated is generally 25 to 39° C., preferably 33 to 39° C., for animal cells. The $CO_2$ concentration is generally 4 to 10% by volume in the culture atmosphere, and 4 to 6% by volume is preferable. The culture period is generally 3 to 35 days, which may be freely set according to the object of the culture. The culture temperature for plant cells is generally 20 to 30° C. and, when light is necessary, they can be cultured under illuminance conditions of illuminance 2000-8000 lux. The culture period is generally 3 to 70 days, which may be freely set according to the object of the culture.

In the culture method of the present invention, culture tools generally used for culturing cells and tissues such as schale, flask, plastic bag, Teflon (registered trade mark) bag, dish, schale, dish for tissue culture, multidish, microplate, microwell plate, multiplate, multiwell plate, chamber slide, tube, tray, culture bag, roller bottle and the like can be used.

The cells and/or tissues can also be cultured by automatically conducting cell seeding, medium exchange, cell image capturing, and recovery of cultured cells, under a mechanical control and under a closed environment while controlling pH, temperature, oxygen concentration and the like and using a bioreactor and an automatic incubator capable of high density culture. As a method for supplying a new medium and feeding the required substances to the cells and/or tissues during the culture using such apparatuses, fed-batch culture, continuous culture and perfusion culture are available, and all these methods can be used for the culture method in the present invention.

Those of ordinary skill in the art can freely select the form and state of the cells or tissues to be cultured in the present invention. Specific preferable examples thereof include, but are not particularly limited to, a state in which the cells or tissues are singly dispersed in the medium composition, a state in which the cells or tissues are attached to the surface of a carrier, a state in which the cells or tissues are embedded inside a carrier, a state in which plural cells assemble and form cell aggregates (spheres), or a state in which two or more kinds of cells assemble and form cell aggregates (spheres), and the like. Among these states, the state with forming cell aggregates (spheres) can be mentioned as a preferable state to be cultured by the culture method of the present invention, since cell-cell interactions and cell structures close to those in the in vivo environment are reconstructed, long-term culture can be performed while maintaining the cell function, and also cell recovery is relatively easy.

As a carrier to support the cells and/or tissues on the surface, microcarrier composed of various polymers, glass bead, ceramic bead and the like can be mentioned. The diameter of the carrier is several tens of micrometers to several hundreds of micrometers, more preferably 100 μm to 200 μm, and its specific gravity is preferably close to 1, more preferably 0.9-1.2, particularly preferably about 1.0. Using the medium composition of the present invention, a carrier supporting cells or tissues on the surface allows for uniform dispersion even without an operation of shaking and the like. As a result, the object cells or tissues can be cultured without losing cell function. The cells or tissues cultured by the method of the present invention can be collected by performing centrifugation and filtration treatment while the cells or tissues are supported by the carrier after the culture. The cells or tissues cultured by this method can be collected by removing them from the carrier by using various chelating agents, a heat treatment, or an enzyme.

When cells or tissues are embedded inside a carrier, materials composed of various polymers can be selected as the carrier. Using the medium composition of the present invention allows a carrier having the cells or tissues embedded therein to uniformly disperse even without an operation of stirring and the like. As a result, the object cells or tissues can be cultured without losing cell function. The cells and/or tissues cultured by the method of the present invention can be collected by performing centrifugation and filtration treatment while the cells and/or tissues are embedded in the carrier after the culture. The cells or tissues cultured by this method can be collected by dispersing them by decomposing the carrier by a treatment using various chelating agents, heat, an enzyme and the like.

A method for forming a cell aggregate (sphere) is not particularly limited, and can be appropriately selected by those of ordinary skill in the art. Examples thereof include a method using a container having a cell non-adhesive surface, hanging drop method, gyratory culture method, three-dimensional scaffold method, centrifugation method, a method using coagulation by an electric field or magnetic field and the like. Furthermore, a sphere can also be formed using the medium composition of the present invention. For example, the object cells are uniformly dispersed in a single cell state in the medium composition of the present invention, cultured and proliferated for 3 days to 10 days by standing, whereby a sphere of the cells can be prepared. Sphere can maintain proliferative capacity for not less than 10 days, preferably not less than 13 days, more preferably not less than 30 days, by continuing static suspension culture in the medium composition of the present invention. By regularly further performing, during the static suspension culture, mechanical division, or a single cell-forming treatment and coagulation, the proliferative capacity can be maintained substantially infinitely. Using the medium composition of the present invention, uniform dispersion in a medium can be afforded even without an operation of shaking and the like. As a result, the object cells can be cultured as a sphere without losing cell function.

The medium composition of the present invention affords an effect of suspending cells or tissues. Using the medium composition of the present invention, a more increased amount of the cells or tissues per a given volume can be cultured as compared to a monolayer culture. In a conventional suspension culture method accompanying rotation or shaking operation, the proliferation rate and recovery rate of the cells or tissues may become low, or the function of the cells may be impaired since a shear force acts on the cells or tissues. Using the medium composition of the present invention, the cells or tissues can be uniformly dispersed in the medium composition without an operation such as shaking and the like, and can obtain the object cells and/or tissues easily in a large amount without loss of the cell function. In addition, when cells or tissues are cultured in suspension in a conventional gel medium, observation and recovery of the cells or tissues are sometimes difficult, and the function thereof is sometimes impaired during recovery. However, using the medium composition of the present invention, the cells or tissues can be cultured in suspension, observed and recovered without impairing the function thereof. In addition, a conventional gel medium sometimes shows high viscosity that makes it difficult to exchange the medium. However, since the medium composition of the present invention has low viscosity, it can be exchanged easily with a pipette, pump and the like.

The medium composition of the present invention contains a given amount of alginic acid or a salt thereof in addition to deacylated gellan gum or a salt thereof. The alginic acid or a salt thereof suppresses bundling of deacylated gellan gum. Thus, using the medium composition of the present invention, the equivalent property of suspending cells or tissues during static culture is maintained, the property is rapidly lost by an operation to apply a shear force with addition of a chelating agent as necessary, the cell recovery rate by a centrifugation operation increases strikingly and therefore, the loss of cells during passage can be minimized, as compared to use of a control medium composition for suspension culture free of alginic acid or a salt thereof and containing deacylated gellan gum or a salt thereof.

The medium composition in the present invention can be used as a reagent for the study of cells since cells or tissues can be grown efficiently using the culture method of the present invention. For example, when a factor controlling the differentiation and proliferation of cells and tissues is to be elucidated, cells and the object factor are cocultured, and the number and kind of cells, and changes in the cell surface differentiation markers or expressed genes are analyzed. In this case, using the medium composition of the present invention, the number of the analysis target cells can be efficiently amplified, and efficiently recovered as well.

Isolation Method of Cells or Tissues

The present invention provides a method for efficiently isolating a cell or tissue from a culture preparation of cells or tissues containing the above-mentioned medium composition of the present invention, and the cells or tissues. The isolation method of the present invention characteristically applies a shear force to the culture preparation.

As mentioned above, a three-dimensional network (amorphous structure) is formed by an assembly of deacylated gellan gum or a salt thereof, and alginic acid or a salt thereof via a metal cation (e.g., divalent metal cation such as calcium ion and the like) in the medium composition of the present invention. When cells or tissues are cultured in the medium composition of the present invention, the cells or tissues suspended in the medium composition are trapped in the three-dimensional network and do not form sediments. Therefore, the cells or tissues can be cultured while being uniformly dispersed in a suspended state (static suspension culture) without the need for shaking, rotational manipulation and the like. On the other hand, the three-dimensional network containing alginic acid or a salt thereof is vulnerable to a shear force and, when a chelating agent is added as necessary to a culture preparation of cells or tissues containing the medium composition of the present invention, and the cells or tissues, and a shear force sufficient to destroy the three-dimensional network is applied thereto, the property to suspend cells or tissues based on the three-dimensional network is rapidly lost, and the cells or tissues easily form sediments due to gravity. When the culture preparation in this state is centrifuged, the cells or tissues contained therein easily form sediments, and the cells or tissues can be isolated by removing the medium composition in the supernatant.

The operation to apply a shear force to a culture preparation is not particularly limited as long as a three-dimensional network (amorphous structure) formed by an assembly of deacylated gellan gum or a salt thereof, and alginic acid or a salt thereof via a metal cation (e.g., divalent metal cation such as calcium ion and the like) can be destroyed. For example, pipetting, filter filtration, stirring, ultrasonication and the like can be mentioned.

To apply a sufficient shear force to the culture preparation, pipetting is preferably performed using a pipette with a comparatively narrow tip (inner diameter of tip is, for example, not more than 5 mm, preferably 0.1-3.0 mm, more preferably 0.5-2.0 mm).

To rapidly stir the culture preparation as a whole, it is preferable to suck and discharge, for example, not less than 1%, preferably not less than 10%, more preferably not less than 20%, further preferably not less than 30%, further more preferably not less than 50%, of the volume of the culture preparation by one operation.

To apply a sufficient shear force to the culture preparation, for example, it is preferable to perform a sucking and/or discharging operation at a flow rate of not less than 1 ml/sec, preferably 2-20 ml/sec, more preferably 5-10 ml/sec.

The number of times of pipetting is not particularly limited as long as it is sufficient to destroy the above-mentioned three-dimensional network. Generally, pipetting is continuously performed not less than one time, preferably not less than 3 times, more preferably not less than 5 times. The more the number of times of pipetting is, the more certainly the above-mentioned three-dimensional network is destroyed and a higher number is preferable. There is no theoretical upper limit thereof. However, when the number of times of pipetting is too many, the survival rate of the cells or tissues decreases. Thus, the number is preferably set to generally not more than 50, preferably not more than 20, more preferably not more than 15. The number of times of pipetting is generally 1-50, preferably 3-20, more preferably 5-15.

The size of the fine pores in the filter (pore size) is not particularly limited as long as it is within the range capable of destroying the above-mentioned three-dimensional network. It is generally not more than 500 µm, preferably not more than 200 µm, more preferably not more than 100 µm. The smaller the pore size is, the more strongly the shear force acts on the culture preparation, and the more certainly the above-mentioned three-dimensional network is destroyed. When it is too small, the medium composition cannot pass through the filter with ease. Thus, the size of the fine pores in the filter (pore size) is generally not less than 5 µm, preferably not less than 10 µm, more preferably not less than 20 µm, further preferably not less than 40 µm.

The pore diameter of the filter is preferably one that permits cells or tissues in the culture preparation to pass through. Here, the "size that permits cells or tissues to pass through" means a size that allows passage of cells or tissues while maintaining survival. For example, the "size that permits cells or tissues to pass through" encompasses not only when the pore diameter of the filter is larger than the diameter of the cells or tissues to be cultured but also an embodiment in which a cell aggregate, sphere or tissue in the culture preparation passes through a filter having a pore diameter smaller than the diameter thereof, whereby it is divided into multiple cells, cell aggregates, spheres or tissues while maintaining survival. While the size of the cell cannot be defined unconditionally since it depends on the kind of the cell, since a general cell having a diameter of about 7.5-20 µm can easily pass through a filter having a pore diameter of not less than 20 µm, preferably 40 µm, in a single cell state while maintaining good survivability. Therefore, to efficiently destroy the above-mentioned three-dimensional network while maintaining good survivability of the cells or tissues, the pore size of the filter is, for example, 20-200 µm, preferably 40-100 µm.

Examples of the material of the filter include, but are not particularly limited to, polyethylene, polypropylene, polyamide (nylon), polysulphone, polypropylene, acryl, polylactic acid, cellulose mixed ester, polycarbonate, polyester, glass and the like. While the properties such as polarity, chargeability, hydrophilicity and the like vary depending on the material, the correlation between these properties and the recovery rate is weak, and a good recovery rate is expected irrespective of the material used. Polyamide (nylon), polyethylene, polyester, glass and the like are preferable from the aspects of easy availability and the like.

As these filters, commercially available products may be used, and concrete examples thereof include CellTrics filter (trade mark) manufactured by Partec: pore diameter 5 µm (model number 06-04-004-2323), 10 µm (model number 06-04-004-2324), 20 µm (model number 06-04-004-2325), 30 µm (model number 06-04-004-2326), 50 µm (model number 06-04-004-2327), 100 µm (model number 06-04-004-2328) and 150 µm (model number 06-04-004-2329), Cell Strainer (trade mark) manufactured by Becton, Dickinson and Company: pore diameter 40 µm (model number 352340), 70 µm (model number 352350) and 100 µm (model number 352360), Filcon S (trade mark) manufactured by AS ONE: pore diameter 20 µm (model number 2-7211-01), 30 µm (model number 2-7211-02), 50 µm (model number 2-7211-03), 70 µm (model number 2-7211-04), 100 µm (model number 2-7211-05) and 200 µm (model number 2-7211-06) and the like.

While the number of passages through the filter may be one, it is possible to improve the recovery rate of cells or tissues by passing them through the filter multiple times as necessary. The number of passages through the filter is generally 1-10.

For passing through a filter multiple times, an operation including passing a culture preparation of cells or tissues through a single filter and collecting the passed suspension may be carried out a plurality of times, or a culture preparation of cells or tissues may be passed through a multiple filter containing a plurality of filter membranes (e.g., 3-5 filter membranes) layered together. The use of a multiple layered filter is advantageous from the viewpoint of operation efficiency. For passage through a filter multiple times, a plurality of filters having the same pore diameter may be used, or a plurality of filters having different pore diameters may be used in combination. Preferably, a plurality of filters (e.g., 3-5 filters) having the same pore diameter (e.g., 40-100 µm) are stacked and used.

Examples of the stirring operation include vortex, mixing by inverting, magnetic stirrer, paddle and the like. The speed of vortex is, for example, 200-3,000 rpm.

When a shear force is applied to a culture preparation, a chelating agent may be added as necessary to the culture preparation. By adding a chelating agent, a metal cation (preferably divalent metal cations such as calcium ion, magnesium ion and the like) is removed from the above-mentioned three-dimensional network contained in the medium composition, and the binding of polysaccharides (deacylated gellan gum or a salt thereof, and alginic acid or a salt thereof) with each other via the metal cation in the three-dimensional network becomes loose and the three-dimensional network is partially destroyed, whereby the recovery rate of the cells or tissues is expected to be improved.

While the chelating agent is not particularly limited as long as it is a compound capable of forming a complex with a divalent metal cation such as calcium ion, magnesium ion and the like (preferably, calcium ion). Examples thereof include citric acid or a salt thereof (e.g., trisodium citrate); EDTA or a salt thereof (e.g., sodium edetates such as EDTA2Na, EDTA3Na, EDTA4Na and the like); salts of hydroxyethylethylenediamine triacetic acid such as HEDTA3Na and the like; EGTA or a salt thereof; pentetate (salts of diethylenetriamine pentaacetic acid); phytic acid; phosphonic acid such as etidronic acid and the like and salts thereof including sodium salt; sodium oxalate; polyamino acids such as polyaspartic acid, polyglutamic acid and the like; sodium polyphosphate; sodium metaphosphate; phosphoric acid; alanine; dihydroxyethylglycine; gluconic acid; ascorbic acid; succinic acid; tartaric acid and the like. To improve recovery rates of cells or tissues, citric acid or a salt thereof (e.g., trisodium citrate) or EDTA or a salt thereof (e.g., sodium edetates such as EDTA2Na, EDTA3Na, EDTA4Na and the like) is preferable. Two or more kinds of the chelating agents can also be used in a mixture. While the combination of chelating agent is not particularly limited, for example, a combination of citric acid or a salt thereof (e.g., trisodium citrate) and EDTA or a salt thereof (e.g., sodium edetates such as EDTA2Na, EDTA3Na, EDTA4Na and the like) can be mentioned.

The amount of a chelating agent to be added is an amount capable of loosening the binding of polysaccharides (deacylated gellan gum or a salt thereof, and alginic acid or a salt thereof) with each other via the metal cation in the three-dimensional network.

For example, in the case of citric acid or a salt thereof (e.g., trisodium citrate), it is generally not less than 0.001 w/v %, preferably, not less than 0.005 w/v %, as the final concentration immediately after addition. Theoretically, the upper limit is a saturated concentration of citric acid or a salt thereof. When the concentration is too high, an influence on the survival of cells or tissues is feared. Therefore, it is generally not more than 0.2 w/v %, more preferably not more than 0.1 w/v %.

In the case of EDTA or a salt (e.g., sodium edetates such as EDTA2Na, EDTA3Na, EDTA4Na and the like), generally, the final concentration immediately after addition is not less than 0.001 w/v %, preferably not less than 0.005 w/v %. Theoretically, the upper limit is a saturated concentration of EDTA or a salt thereof. When the concentration is too high, an influence on the survival of cells or tissues is feared. Therefore, it is generally not more than 0.2 w/v %, more preferably not more than 0.1 w/v %.

After addition of the chelating agent to the aforementioned culture preparation, the obtained mixture is preferably stirred well by an operation to apply a shear force to the aforementioned culture preparation so that the chelating agent will be uniform.

After the aforementioned pre-treatment step, the resultant mixture containing cells or tissues is subjected to centrifugation to precipitate the cells or tissues and fractions other than the cells or tissues (e.g., the medium composition of the present invention in the supernatant) are removed, whereby the cells and/or tissues can be finally isolated from the culture preparation of the cells or tissues. Techniques for precipitating cells or tissues by centrifugation are well known to those of ordinary skill in the art and appropriate conditions can be set by those of ordinary skill in the art according to the type of cell or tissue. In general, cells or tissues can be precipitated and separated from the supernatant by centrifugation with a centrifugal force of about 10-400G.

As mentioned above, the loss of the effect of maintaining the suspended state of the cells or tissues by a shear force by pipetting, filter filtration and the like is a reversible reaction. Therefore, it is preferable to perform centrifugation after the above-mentioned pre-treatment step and before regeneration of the three-dimensional network (amorphous structure). For example, centrifugation is started within 60 min, preferably 30 min, more preferably 10 min, after completion of the above-mentioned pre-treatment step.

Reagent for Isolating Cells or Tissues (Kit)

The present invention also provides a reagent (kit) for isolating cells or tissues from a culture preparation of the cells or tissues which contains the above-mentioned medium composition of the present invention, and the cells or tissues, containing the above-mentioned filter.

The reagent of the present invention may further contain the above-mentioned chelating agent.

By using the reagent of the present invention, cells or tissues can be easily isolated from a culture preparation of the cells or tissues containing the above-mentioned medium composition of the present invention, and the cells or tissues, by performing the above-mentioned isolating method of the present invention. The definition of each term is as described in the aforementioned "Method for isolating cells or tissues".

The reagent of the present invention may further contain deacylated gellan gum or a salt thereof and alginic acid or a salt thereof in combination for preparing the above-mentioned medium composition of the present invention. Using the reagent of the present invention in such embodiment, the user can prepare the above-mentioned medium composition of the present invention by using deacylated gellan gum or a salt thereof and alginic acid or a salt thereof, culture the desired cells or tissues in suspension in the medium composition, and isolate the cells or tissues from the obtained culture preparation of the cells or tissues by the above-mentioned isolation method of the present invention.

The deacylated gellan gum or a salt thereof, and alginic acid or a salt thereof may be contained as an isolated compound or an aqueous solution in the reagent of the present invention, or may be contained in an embodiment of the above-mentioned medium composition of the present invention in the reagent of the present invention.

The present invention is explained in more detail in the following by concretely describing Examples of the medium composition of the present invention, which are not to be construed as limitative. [Examples]

[Experimental Example 1] Production of Polysaccharide Mixture 1 part by mass or 2 parts by mass of sodium alginate (ALG) and 99 parts by mass or 98 parts by mass of purified water were added to a glass medium bottle, and the mixture was subjected to an autoclave sterilization treatment (121° C., 20 min) to give 1 mass % or 2 mass % concentration of an aqueous ALG solution.

In the same manner, 1 mass % concentration and 2 mass % concentration of aqueous deacylated gellan gum (DAG) (KELCOGEL CG-LA, manufactured by SANSHO Co., Ltd.) solutions were produced.

Given amounts of the aqueous ALG solution and aqueous DAG solution were fractionated into microtubes and carefully mixed by pipetting and homogenized using a disposable syringe with a syringe needle to give a polysaccharide mixture.

[Experimental Example 2] Production of Medium Composition (1) Production of Medium Composition Using Vortex Mixer A given amount of a medium was dispensed to a conical tube (SUMITOMO BAKELITE CO., LTD. 15 mL, 50 mL or 225 mL centrifuge tube) and they were kept under stirring by a vortex mixer while left open. To the medium was vigorously added a given amount of a polysaccharide mixture from a disposable syringe (TERUMO CORPORATION TERUMO syringe) with a syringe needle (Fuchigami kikai, FN5200) and filled with the polysaccharide mixture, whereby a medium composition was produced.
(2) Production of Medium Composition Using Medium Production Kit (Nissan Chemical Industries, FCeM™-Series Preparation Kit)

A given amount of a medium was dispensed to a conical tube (SUMITOMO BAKELITE CO., LTD. 50 mL centrifuge tube) and an adapter cap, which was a constitution of the kit, was set. The tip of a disposable syringe filled with a given amount of a polysaccharide mixture was fitted into the cylindrical portion of the adapter cap to establish connection. The plunger of the syringe was pushed manually to vigorously inject the polysaccharide mixture in the syringe into the container, allowing contact with the medium, whereby a medium composition was produced.

[Experimental Example 3] Confirmation of Suspending Action

To the medium composition produced in Experimental Example 2 were added polystyrene beads (diameter 500-600 μm, manufactured by Polysciences Inc.) for reproducing suspending cells simulatively and the mixture was stirred. At 10 min from discontinuation of stirring, the dispersion state of the beads in the liquid was confirmed by visual observation. When the sufficient amount of the structure formed by crosslinking of DAG and ALG via a divalent metal cation ($Ca^{2+}$ etc.) is dispersed appropriately finely in the liquid, the beads are also dispersed and suspending in the liquid. On the other hand, when the structure is not sufficiently dispersed, the beads also form sediments accordingly. The dispersion state of the beads is shown with ○ when the beads were preferably dispersed and suspended, Δ when the beads were dispersed with partial formation of sediment, and x when all beads formed sediment.
(1) Suspending Action Using DAG and ALG (1:1)

[Experimental Example 4] Cell Recovery by Pipetting

Normal human neonatal foreskin skin fibroblasts (NHDF, KURABO INDUSTRIES LTD.) in the logarithmic growth phase ($1800 \times 10^4$ cells) were prepared and dispensed by $300 \times 10^4$ cells. After centrifugation (300×g, 3 min), the supernatant was removed, medium compositions containing DAG and ALG (total concentration 0.015 (w/v) %) at various ratios (Examples C369 to C373 in Table 3) were added by 30 mL and the mixtures were gently stirred to produce cell suspensions ($10 \times 10^4$ cells/mL). To a 24-well cell culture plate (manufactured by SUMITOMO BAKELITE CO., LTD.) was added a cell suspension ($10 \times 10^4$ cells) by 1 mL per 1 well, and the cells were cultured under 37° C., 5% carbon dioxide gas conditions for 1 week. After culturing, the cell concentration of the cell suspension was measured by a cell counter (TC-20, BIO-RAD), the suspension was transferred to a 1.5 mL microtube and homogenized by 20 times of pipetting using a micropipette (manufactured by Thermo Scientific, clip chip 1000 μL) set to suction/discharge volume 0.2 mL. Thereafter, centrifugation (300×g, 3 min) was performed and the supernatant (1.1 mL) was removed. The cells were resuspended by adding 10% fetal bovine serum-containing DMEM-LG (0.9 mL), and the amount of ATP contained in the cells was quantified by a plate reader (manufactured by Tecan Japan Co., Ltd.) and using CellTiter-Glo (Promega Corporation). With the RLU value obtained by measuring the suspension of the cultured cells before the cell recovery operation as the standard (cell recovery rate 100%), the RLU values obtained by a cell recovery operation with the addition of a suspension inhibitor were compared and the cell recovery rate was calculated. The above test was performed 3 times each, and the mean thereof is shown in the Table.

TABLE 1

| | | medium | | polysaccharide mixture | | | | | | |
|---|---|---|---|---|---|---|---|---|---|---|
| No. | kind | temperature [° C.] | amount added [mL] | 2% DAG [μL] | 1% ALG [μL] | distilled water [μL] | amount added [μL] | addition method | final concentration % DAG/ALG | suspending action |
| B358 | DMEM-low | 4 | 5 | 250 | 500 | 250 | 90 | vortex | 0.009/0.009 | ○ |
| B359 | ↑ | 4 | 5 | ↑ | ↑ | ↑ | 80 | ↑ | 0.008/0.008 | ○ |
| B360 | ↑ | 4 | 5 | ↑ | ↑ | ↑ | 70 | ↑ | 0.007/0.007 | ○ |
| B361 | ↑ | 4 | 5 | ↑ | ↑ | ↑ | 60 | ↑ | 0.006/0.006 | ○ |
| B362 | ↑ | 4 | 5 | ↑ | ↑ | ↑ | 50 | ↑ | 0.005/0.005 | Δ |

(2) Suspending Action Using DAG and ALG (0.5:1)

TABLE 2

| | | medium | | polysaccharide mixture | | | | | |
|---|---|---|---|---|---|---|---|---|---|
| No. | kind | temperature [° C.] | amount added [mL] | 1% DAG [μL] | 2% ALG [μL] | amount added [μL] | addition method | final concentration % DAG/ALG | suspending action |
| B363 | DMEM-low | 4 | 5 | 500 | 500 | 75 | vortex | 0.0075/0.015 | ○ |
| B364 | ↑ | 4 | 5 | ↑ | ↑ | 65 | ↑ | 0.0065/0.013 | ○ |
| B365 | ↑ | 4 | 5 | ↑ | ↑ | 55 | ↑ | 0.0055/0.011 | ○ |
| B366 | ↑ | 4 | 5 | ↑ | ↑ | 50 | ↑ | 0.005/0.01 | ○ |
| B367 | ↑ | 4 | 5 | ↑ | ↑ | 45 | ↑ | 0.0045/0.009 | ○ |

TABLE 3

| | | Example | | | | |
|---|---|---|---|---|---|---|
| | | C369 | C370 | C371 | C372 | C373 |
| concentration % in medium | ALG | 0.01 | 0.0105 | 0.011 | 0.0115 | 0.012 |
| | DAG | 0.005 | 0.0045 | 0.004 | 0.0035 | 0.003 |
| cell recovery rate % | | 69.6 | 57.1 | 79.4 | 86.3 | 99.4 |

[Experimental Example 5] Study of Number of Pipettings

Normal human neonatal foreskin skin fibroblasts (NHDF, KURABO INDUSTRIES LTD.) in the logarithmic growth phase ($1440 \times 10^4$ cells) were prepared, suspended in the medium composition (48 mL) of Example C371 in Table 3, dispensed by $30 \times 10^4$ cells (1 mL) to a 24-well cell culture plate (manufactured by SUMITOMO BAKELITE CO., LTD.), and cultured under 37° C., 5% carbon dioxide gas conditions for 3 days. After culturing, the cell concentration of the cell suspension was measured by a cell counter (TC-20, BIO-RAD), the suspension was transferred to a 1.5 mL microtube and pipetted a given number of times using a micropipette (manufactured by Thermo Scientific, clip chip 1000 µL) set to suction/discharge volume 0.2 mL. Thereafter, centrifugation (300×g, 3 min) was performed and the supernatant (1.1 mL) was removed. The cells were resuspended by adding 10% fetal bovine serum-containing DMEM-LG (0.9 mL), and the amount of ATP contained in the cells was quantified by a plate reader (manufactured by Tecan Japan Co., Ltd.) and using CellTiter-Glo (Promega Corporation), and the cell recovery rate was calculated. The above test was performed 5 times each, and the mean thereof is shown in the Table.

TABLE 4

| | number of pipettings | | | | |
|---|---|---|---|---|---|
| | 3 | 5 | 10 | 15 | 20 |
| cell recovery rate % | 44.2 | 69.9 | 70.6 | 68.3 | 75.9 |

[Experimental Example 6] Addition of Chelating Agent

Normal human neonatal foreskin skin fibroblasts (NHDF, KURABO INDUSTRIES LTD.) in the logarithmic growth phase ($450 \times 10^4$ cells) were prepared, suspended in the medium composition (15 mL) of Example C371 in Table 3, dispensed by $30 \times 10^4$ cells (1 mL) to a 24-well cell culture plate (manufactured by SUMITOMO BAKELITE CO., LTD.), and cultured under 37° C., 5% carbon dioxide gas conditions for 3 days. After culturing, the cell concentration of the cell suspension was measured by a cell counter (TC-20, BIO-RAD), the suspension was transferred to a 1.5 mL microtube, a given amount of a chelating agent (aqueous mixed solution of EDTA-2Na 0.033 (w/v) % and sodium citrate 0.007 (w/v) %) (0 to 0.1 mL) was added, and pipetted 0 or 10 times using a micropipette (manufactured by Thermo Scientific, clip chip 1000 µL) set to suction/discharge volume 0.2 mL. Thereafter, centrifugation (300×g, 3 min) was performed and the supernatant (1.1 mL) was removed. The cells were resuspended by adding 10% fetal bovine serum-containing DMEM-LG (0.9 mL), and the amount of ATP contained in the cells was quantified by a plate reader (manufactured by Tecan Japan Co., Ltd.) and using CellTiter-Glo (Promega Corporation), and the cell recovery rate was calculated. The above test was performed 3 times each, and the mean thereof is shown in the Table.

TABLE 5

| number of pipettings | 0 | 10 | 10 | 10 |
|---|---|---|---|---|
| amount of chelating agent added mL | 0 | 0 | 0.05 | 0.1 |
| cell recovery rate % | 6.1 | 91.3 | 89.1 | 89.6 |

[Experimental Example 7] Proliferation of Jurkat Cell

Normal human T-cell leukemia-derived cells (Jurkat E6.1, DS Pharma Biomedical Co., Ltd.) in the logarithmic growth phase ($240 \times 10^4$ cells) were prepared, centrifuged by $40 \times 10^4$ cells (300×g, 3 min), and the supernatant was removed. Medium compositions containing DAG and ALG (mass ratio 1:0.5) at various concentrations (Examples DHb020 to DHb023 in Table 6), and a medium composition containing DAG and not containing ALG (Comparative Example DHb024 in Table 6) were added by 8 mL and the mixtures were gently stirred to produce cell suspensions ($5 \times 10^4$ cells/mL). To a 96-well U-bottom cell culture plate (manufactured by SUMITOMO BAKELITE CO., LTD., MS-309UR) was added a cell suspension ($0.5 \times 10^4$ cells) by 0.1 mL per 1 well, and the cells were cultured under 37° C., 5% carbon dioxide gas conditions for 1 or 4 days. With the cell numbers before and after culturing as the amount of ATP contained in the cells, they were compared by a plate reader (manufactured by Tecan Japan Co., Ltd., infinite M200PRO) and using CellTiter-Glo Luminescent Cell Viability Assay (Promega KK, G7571). The above test was performed 4 times each, and the mean thereof is shown in the Table.

TABLE 6

| | | concentration % in medium | | RLU | | |
|---|---|---|---|---|---|---|
| | | DAG | ALG | before culturing | one day from culturing | 4 days from culturing |
| Comparative Example | DHb024 | 0.020 | 0 | 156639 | 318811 | 1755495 |
| Example | DHb020 | 0.0037 | 0.0073 | 169680 | 351910 | 2068701 |
| | DHb021 | 0.0047 | 0.0093 | 177597 | 362442 | 2107969 |
| | DHb022 | 0.0057 | 0.0113 | 171730 | 313565 | 1973738 |
| | DHb023 | 0.0067 | 0.0133 | 191724 | 332460 | 2016689 |

As a result of evaluation, cell proliferation property equivalent to Comparative Example was achieved even when the medium composition of the present invention was used.

[Experimental Example 8] A549 Cell Proliferation

Human alveolar basal epithelial adenocarcinoma cells (A549, DS Pharma Biomedical Co., Ltd.) in the logarithmic growth phase ($86.4 \times 10^4$ cells) were prepared, centrifuged (300×g, 3 min), and the supernatant was removed. Medium compositions containing DAG and ALG (mass ratio 1:0.5) at various concentrations (Example E041 and Examples E045, E047, E048 in Table 7), and a medium composition containing DAG and not containing ALG (Comparative Example E049 in Table 7) were added by 8 mL and the mixtures were gently stirred to produce cell suspensions ($5 \times 10^4$ cells/mL). To a 96-well U-bottom cell culture plate (manufactured by SUMITOMO BAKELITE CO., LTD., MS-309UR) was added a cell suspension ($0.5 \times 10^4$ cells) by 0.1 mL per 1 well, and the cells were cultured under 37° C., 5% carbon dioxide gas conditions for 1 or 4 days. With the cell numbers before and after culturing as the amount of ATP contained in the cells, they were compared by a plate reader (manufactured by Tecan Japan Co., Ltd., infinite M200PRO) and using CellTiter-Glo Luminescent Cell Viability Assay (Promega KK, G7571). The above test was performed 6 times each, and the mean thereof is shown in the Table.

TABLE 7

| | | concentration % in medium | | | RLU | | |
|---|---|---|---|---|---|---|---|
| | | DAG | ALG | before culturing | one day from culturing | 4 days from culturing | 7 days from culturing |
| Comparative Example | E049 | 0.015 | 0 | 100639 | 114674 | 593527 | 1706412 |
| Example | E045 | 0.002 | 0.004 | 109473 | 127249 | 676181 | 1689925 |
| | E041 | 0.003 | 0.006 | 99532 | 121673 | 595366 | 1738593 |
| | E047 | 0.004 | 0.008 | 101544 | 118188 | 570577 | 1662464 |
| | E048 | 0.005 | 0.010 | 102446 | 120400 | 584303 | 1659677 |

As a result of evaluation, cell proliferation property equivalent to Comparative Example was achieved even when the medium composition of the present invention was used.

[Experimental Example 9] Cell Recovery on 10 mL Scale

In the medium composition (200 mL) of Example E041 in Table 7 were seeded A549 cells at $10 \times 10^4$ cells/mL and the cells were cultured under 37° C., 5% carbon dioxide gas conditions for 2 days. After culturing, the cell suspension was fractionated by 10 mL and a chelating agent (aqueous mixed solution of EDTA-2Na 0.033 (w/v) % and sodium citrate 0.007 (w/v) %) (1 mL) was added. The mixture was immediately passed through a cell strainer (40 μm, 70 μm, 100 μm, Falcon® cell strainer) and centrifuged (3 min) under various conditions (50×g, 100×g, 300×g, g: gravitational acceleration). With the aforementioned cell numbers before and after cell recovery operation as the amount of ATP contained in the cells, they were compared by a plate reader (manufactured by Tecan Japan Co., Ltd., infinite M200PRO) and using CellTiter-Glo Luminescent Cell Viability Assay (Promega KK, G7571).

TABLE 8

| | gravitational acceleration | cell recovery rate % | | |
|---|---|---|---|---|
| | | 50 | 100 | 300 |
| cell strainer fine pore size | 40 μm | 73.3 | 92.7 | 96.2 |
| | 70 μm | — | — | 98.6 |
| | 100 μm | — | — | 96.4 |

As a result of evaluation, it was shown that the medium composition of the present invention can also achieve a high cell recovery rate by passing through a mesh (cell strainer) instead of a pipetting operation.

INDUSTRIAL APPLICABILITY

The medium composition of the present invention provides an effect of maintaining the suspended state of cells or tissues and has property of rapidly losing the effect by adding a chelating agent as necessary, and applying a shear force by pipetting, filter filtration and the like. Therefore, using the medium composition of the present invention, cells and tissues can be suspension cultured (preferably, static suspension culture), and the cells and tissues can be recovered at a high recovery rate from the obtained culture preparation.

The contents disclosed in any publication stated in the present specification, including patents, patent applications and scientific literatures, are hereby incorporated in their entireties by reference, to the extent that they have been disclosed herein.

This application is based on a patent application No. 2016-046365 filed in Japan (filing date: Mar. 9, 2016), the contents of which are incorporated in full herein.

The invention claimed is:

1. A medium composition permitting culture of a cell or a tissue in suspension containing a three dimensional network, comprising deacylated gellan gum or a salt thereof and alginic acid or a salt thereof, wherein
   a concentration of the deacylated gellan gum or a salt thereof in the medium composition is 0.002-0.01 (w/v) %,
   a concentration of the alginic acid or a salt thereof in the medium composition is 0.004-0.02 (w/v) %,
   a mass ratio of the alginic acid or a salt thereof to the deacylated gellan gum or a salt thereof is from 2 to 4, and
   the three dimensional network is formed by crosslinking of deacylated gellan gum or a salt thereof and alginic acid or a salt thereof via a divalent metal cation.

2. The medium composition according to claim 1, wherein the divalent metal cation is a calcium ion.

3. The medium composition according to claim 1, wherein the alginic acid or a salt thereof is treated by high-pressure vapor sterilization.

4. A cell or tissue culture preparation comprising the medium composition according to claim 1, and a cell or a tissue.

* * * * *